United States Patent
Sundstrom

(10) Patent No.: US 12,429,467 B2
(45) Date of Patent: Sep. 30, 2025

(54) SYSTEMS AND METHODS FOR MEASURING COMPOSITION OF WATER

(71) Applicant: Evoqua Water Technologies LLC, Pittsburgh, PA (US)

(72) Inventor: Glen P. Sundstrom, Rockford, IL (US)

(73) Assignee: Evoqua Water Technologies LLC, Pittsburgh, PA (US)

( * ) Notice: Subject to any disclaimer, the term of this patent is extended or adjusted under 35 U.S.C. 154(b) by 921 days.

(21) Appl. No.: 17/268,450

(22) PCT Filed: Aug. 13, 2019

(86) PCT No.: PCT/US2019/046264
§ 371 (c)(1),
(2) Date: Feb. 12, 2021

(87) PCT Pub. No.: WO2020/036912
PCT Pub. Date: Feb. 20, 2020

(65) Prior Publication Data
US 2021/0181167 A1    Jun. 17, 2021

Related U.S. Application Data

(60) Provisional application No. 62/718,085, filed on Aug. 13, 2018.

(51) Int. Cl.
*C02F 1/00*     (2023.01)
*C02F 1/20*     (2023.01)
(Continued)

(52) U.S. Cl.
CPC ............ *G01N 31/10* (2013.01); *C02F 1/008* (2013.01); *C02F 1/20* (2013.01); *C02F 1/42* (2013.01);
(Continued)

(58) Field of Classification Search
CPC .......... G01N 31/10; G01N 33/18; G01N 1/40; G01N 35/00; C02F 1/008; C02F 1/20;
(Continued)

(56) References Cited

U.S. PATENT DOCUMENTS 4,427,772 A    1/1984   Kodera et al.
6,972,083 B2  12/2005   Desai et al.
(Continued)

FOREIGN PATENT DOCUMENTS

JP    2012061443         3/2012
JP    2012063303 A  *    3/2012
(Continued)

OTHER PUBLICATIONS

Supplementary European Search Report, for corresponding European Patent Application No. 19849092.2, mailed Apr. 7, 2022.
(Continued)

*Primary Examiner* — Neil N Turk

(57) ABSTRACT

A method of determining composition of an aqueous solution is disclosed. The method includes obtaining the aqueous solution, removing oxygen from the aqueous solution, determining concentration of dissolved oxygen, removing hydrogen peroxide from the aqueous solution, and determining concentration of dissolved oxygen. The method includes calculating the difference between the concentrations of dissolved oxygen to determine concentration of hydrogen peroxide. A system for determining composition of an aqueous solution is also disclosed. The system includes a feed line connectable to a source of the aqueous solution, an oxygen removal unit, a hydrogen peroxide removal unit, and dissolved oxygen analyzers.

15 Claims, 7 Drawing Sheets

(51) Int. Cl.
  *C02F 1/42* (2023.01)
  *C02F 1/44* (2023.01)
  *C02F 1/72* (2023.01)
  *G01N 31/10* (2006.01)
  *G01N 33/18* (2006.01)
  *C02F 101/10* (2006.01)
  *C02F 103/04* (2006.01)

(52) U.S. Cl.
  CPC .............. *C02F 1/448* (2013.01); *C02F 1/722* (2013.01); *G01N 33/18* (2013.01); *C02F 2101/10* (2013.01); *C02F 2103/04* (2013.01); *C02F 2209/22* (2013.01)

(58) Field of Classification Search
  CPC ........ C02F 1/42; C02F 1/448; C02F 2101/10; C02F 2103/04; C02F 2209/22
  See application file for complete search history.

(56) References Cited

U.S. PATENT DOCUMENTS

2007/0238188 A1    10/2007    Carr
2009/0127201 A1    5/2009    Kobayashi

FOREIGN PATENT DOCUMENTS

KR    20160011722 A    2/2016
WO    98/30884 A1    7/1998

OTHER PUBLICATIONS

European Office Action in corresponding EP Application No. 19849092.1, mailed Apr. 19, 2022.
International Search Report, corresponding PCT/US2019/46264, dated Nov. 21, 2019.
Carberry, "Peroxide Pre-Oxidation of Recalcitrant Toxic Waste to Enhance Biodegradation," Wat. Sci. Tech. vol. 23, Kyoto, pp. 367-376, 1991.
Rafa, Al-Muhannad, "Notice of Deficiencies", Israeli Patent Application No. 280249, mailed Feb. 8, 2024, 3 pages.
Unknown, "Notice to Submit Response", Korean Patent Application No. 10-2021-7007503, mailed Aug. 26, 2024, 12 pages.

\* cited by examiner

SYSTEMS AND METHODS FOR MEASURING COMPOSITION OF WATER

CROSS-REFERENCE TO RELATED APPLICATIONS

This application is a U.S. national phase application and claims the benefit of priority under 35 U.S.C. § 371, of International (PCT) Patent Application Serial No. PCT/US2019/046264, filed on Aug. 13, 2019, which claims priority under 35 U.S.C. § 119 (e) to U.S. Provisional Application Ser. No. 62/718,085 titled "Method for Measuring Low Levels Hydrogen Peroxide in Water with a High Dissolved Oxygen Background" filed Aug. 13, 2018, each of which is incorporated herein by reference in its entirety for all purposes.

FIELD OF TECHNOLOGY

Aspects and embodiments disclosed herein are generally related to determining composition of aqueous solutions, and more specifically, to systems and methods for measuring low levels of hydrogen peroxide in solution with a dissolved oxygen background.

SUMMARY

In accordance with one aspect, there is provided a method of determining composition of an aqueous solution. The method may comprise obtaining the aqueous solution comprising a concentration of hydrogen peroxide and a concentration of dissolved oxygen. The method may comprise removing oxygen from at least a portion of the aqueous solution to produce a first sample. The method may comprise determining a first sample concentration of dissolved oxygen in the first sample. The method may comprise removing hydrogen peroxide from at least a portion of the first sample to produce a second sample. The method may comprise determining a second sample concentration of dissolved oxygen in the second sample. The method may comprise calculating a difference between the second sample concentration of dissolved oxygen and the first sample concentration of dissolved oxygen to determine the concentration of hydrogen peroxide in the aqueous solution.

In certain embodiments, removing oxygen from the at least a portion of the aqueous solution may comprise directing the at least a portion of the aqueous solution to an oxygen removal process.

The method may comprise directing the at least a portion of the aqueous solution to the oxygen removal process selected from a vacuum degasification process, a gas transfer membrane, an oxygen scavenging media, a vacuum mechanical agitation process, and combinations thereof.

In certain embodiments, removing hydrogen peroxide from the at least a portion of the first sample may comprise directing the at least a portion of the first sample to a hydrogen peroxide destruction process.

In some embodiments, directing the at least a portion of the first sample to the hydrogen peroxide destruction process may comprise directing the at least a portion of the first solution to a catalyst-driven hydrogen peroxide destruction process.

The method may comprise directing the at least a portion of the first solution to the catalyst-driven hydrogen peroxide destruction process selected from a heterogeneous catalyst comprising palladium-doped anion exchange resin, a heterogeneous catalyst comprising a metal immobilized on a substrate, a homogeneous catalyst comprising an enzyme, and combinations thereof.

The method may comprise multiplying the difference between the second sample concentration of dissolved oxygen and the first sample concentration of dissolved oxygen by 2.125 to determine the concentration of hydrogen peroxide in the aqueous solution.

In certain embodiments, at least one of determining the first sample concentration of dissolved oxygen and determining the second sample concentration of dissolved oxygen may comprise directing the first sample or the second sample to at least one dissolved oxygen analyzer.

In certain embodiments, the method may be capable of detecting the concentration of hydrogen peroxide of about 10 ppb or less.

In certain embodiments, the method may be capable of detecting the concentration of hydrogen peroxide of about 2 ppb or less.

In accordance with another aspect, there is provided a system for determining composition of an aqueous solution. The system may comprise a feed line fluidly connectable to a source of the aqueous solution comprising a concentration of hydrogen peroxide and a concentration of dissolved oxygen. The system may comprise an oxygen removal unit having an inlet fluidly connected to the feed line. The system may comprise a first dissolved oxygen analyzer having an inlet fluidly connected to the oxygen removal unit. The system may comprise a hydrogen peroxide removal unit having an inlet fluidly connected to the oxygen removal unit and an outlet fluidly connected to the dissolved oxygen analyzer The system may comprise a first valve positioned between the oxygen removal unit and the first dissolved oxygen analyzer.

The system may comprise a second valve positioned between the hydrogen peroxide removal unit and the first dissolved oxygen analyzer.

The system may comprise a third valve positioned between the hydrogen peroxide removal unit and a discharge outlet. The third valve may be configured to discharge the aqueous solution when the second valve is closed.

In certain embodiments, the first dissolved oxygen analyzer may comprise a display unit configured to display dissolved oxygen concentration.

The system may comprise a control module electrically connected to the first dissolved oxygen analyzer. The control module may be configured to calculate a difference between a first concentration of dissolved oxygen of the aqueous solution upstream from the hydrogen peroxide removal unit and a second concentration of dissolved oxygen of the aqueous solution measured downstream from the hydrogen peroxide removal unit to determine the concentration of hydrogen peroxide in the aqueous solution.

The control module may be capable of determining the concentration of hydrogen peroxide of about 10 ppb or less.

The control module may be capable of determining the concentration of hydrogen peroxide of about 2 ppb or less.

In certain embodiments, the first dissolved oxygen analyzer may comprise a plurality of dissolved oxygen analyzers.

In certain embodiments, the oxygen removal unit may comprise at least one of a vacuum degasification unit, a gas transfer membrane, an oxygen scavenging media, and a vacuum mechanical agitation unit.

In certain embodiments, the hydrogen peroxide removal unit may comprise a catalyst-driven hydrogen peroxide removal unit.

In certain embodiments, the catalyst-driven hydrogen peroxide removal unit may comprise at least one of a heterogeneous catalyst comprising palladium-doped anion exchange resin, a heterogeneous catalyst comprising platinum immobilized on a substrate, and a homogeneous catalyst comprising an enzyme.

The system may comprise a second dissolved oxygen analyzer having an inlet fluidly connected to the hydrogen peroxide removal unit.

The system may comprise a third dissolved oxygen analyzer positioned upstream from the oxygen removal unit.

The system may comprise a fourth valve positioned between the feed line and the oxygen removal unit.

The disclosure contemplates all combinations of any one or more of the foregoing aspects and/or embodiments, as well as combinations with any one or more of the embodiments set forth in the detailed description and any examples.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1A:
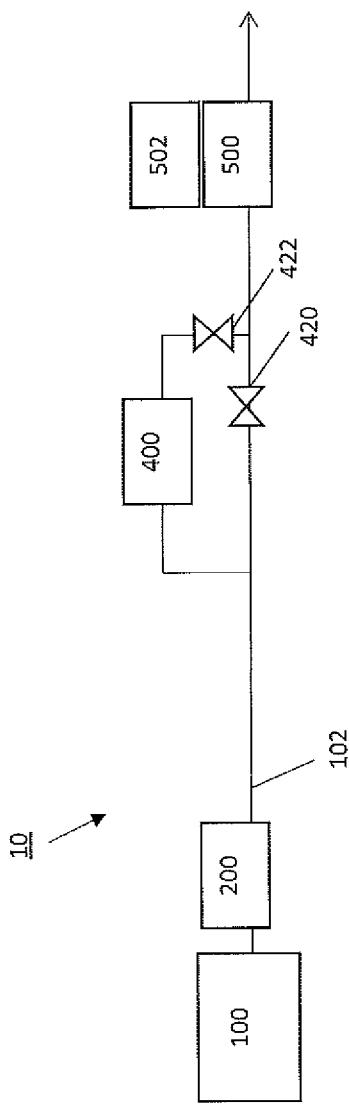
FIG. 1A is a box diagram of a system for determining composition of an aqueous solution, according to one embodiment.

Hydrogen peroxide ($H_2O_2$) is commonly found in process waters, and occasionally introduced as a water treatment additive. Hydrogen peroxide detection methods may be employed whether the hydrogen peroxide is a desirable constituent or an undesirable contaminant of the water. Often, hydrogen peroxide concentrations are carefully controlled to be within tolerance of a target concentration. For instance, the hydrogen peroxide concentration in process waters may be controlled to be within 10 ppb or within 2 ppb of a target concentration. Thus, effective detection methods may be needed to control hydrogen peroxide concentration to be within narrow tolerance of the target threshold.

Hydrogen peroxide may be used as an oxidant in industrial applications. Hydrogen peroxide is typically a stronger oxidant than, for example, chlorine and permanganate. One application of hydrogen peroxide is in advanced oxidation processes employed to remove recalcitrant organic contaminants, such as herbicides and polychlorinated biphenyls (PCB), from wastewaters. For example, water containing organic impurities may be treated by addition of hydrogen peroxide at approximately 1% followed by ultraviolet (UV) exposure. In addition, hydrogen peroxide and ozone ($O_3$) may be used with UV at a field scale to treat ground water contaminated with volatile organic compounds.

The partial oxidation of recalcitrant compounds may also be performed with hydrogen peroxide. For example, chlorinated aromatics may be biodegraded by pre-oxidation with hydrogen peroxide at a molar ratio between 2:1 and 6:1, for example, 4:1. Hydrogen peroxide is typically thermally stable. Hydrogen peroxide may generally be stored on-site. Hydrogen peroxide is typically soluble in water. The use of hydrogen peroxide may reduce mass transfer complications of associated gases.

Hydrogen peroxide may be used in the removal of color, for example, as a bleaching agent in the textile industry. Hydrogen peroxide may be used in the manufacture of paper and during waste paper recycling. Other applications of hydrogen peroxide may include the oxidation of sulfides for odor control, corrosion control of waste pipes, additional oxygen source for overloaded activated sludge plants, and the control of filamentous bulking.

Occasionally, hydrogen peroxide may be an undesirable constituent. The presence of hydrogen peroxide in certain waters may be deleterious. Hydrogen peroxide may be formed as a byproduct during the photolysis of water at 185 nm wavelength UV light. The 185 nm wavelength UV light is commonly used for the reduction of total oxidizable carbon (TOC). In the semiconductor industry, for example, 185 nm wavelength UV may be used to reduce a TOC concentration in ultrapure water to 1 ppb or less. Undesired hydrogen peroxide may be formed in the process.

The photolysis of hydrogen peroxide typically produces hydroxyl radicals (OH·). For instance, the photochemical reduction of $Fe^{3+}$ to $Fe^{2+}$ in the presence of hydrogen peroxide typically increases generation of hydroxyl radicals. Hydroxyl radicals are generally highly oxidizing species and may be undesirable in certain waters.

Hydrogen peroxide is also often used in semiconductor manufacturing processes. For example, hydrogen peroxide may be used to remove organic residues for semiconductor wafer manufacturing. During such processes, hydrogen peroxide typically degrades to oxygen and water, and thus does not contribute contaminants to the solution. It may be desirable to reduce any residual hydrogen peroxide concentration to below 10 ppb. For example, it may be desirable to reduce residual hydrogen peroxide concentration to as low as 2 ppb.

Conventional detection methods for hydrogen peroxide in water may not accurately measure such low hydrogen peroxide concentrations, in particular where there are high background concentrations of other constituents. Conventional methods may further not be capable of performing hydrogen peroxide concentration measurements in-line. For instance, conventional hydrogen peroxide detection test strips may not be employed in-line to detect hydrogen peroxide and are typically capable of detecting 1-50 ppm of hydrogen peroxide in water.

The systems and methods disclosed herein may be used to detect hydrogen peroxide concentrations below about 20 ppb. In certain embodiments, the systems and methods disclosed herein may be used to detect hydrogen peroxide concentrations below about 10 ppb. The systems and methods disclosed herein may be used to detect hydrogen peroxide concentrations of about 12 ppb or less, about 10 ppb or less, about 8 ppb or less, about 6 ppb or less, or about 4 ppb or less. In particular, the systems and methods disclosed herein may be used to detect hydrogen peroxide concentrations as low as about 2 ppb or as low as about 1 ppb.

The concentration of hydrogen peroxide employed or formed in the water processes disclosed herein may be carefully controlled and monitored for efficient and cost effective usage. Conventionally, hydrogen peroxide is monitored by titrimetric, gasometric, electrochemical calorimetric, chemiluminescent, and acoustic methods. Titrimetric methods include, for example, those monitoring methods based on the oxidation of hydrogen peroxide with permanganate, followed by the reduction of the solution with acidic potassium iodide. The results of these monitoring methods may be used to control hydrogen peroxide levels. However, conventional methods of monitoring hydrogen peroxide can be time consuming, sensitive to interference, and have poor lifetime. Thus, these methods may not be so effective for process monitoring and control.

Methods for measuring hydrogen peroxide include adding an enzyme, for example, catalase, to a liquid sample. The sample may be agitated so as to permit the hydrogen peroxide to decompose and oxygen gas to be generated. The oxygen gas may displace a sample volume for the measurement of the sample. The sample volume may be, directly or indirectly, converted to a value representing the amount of hydrogen peroxide present. A catalyst may be used to remove and/or measure hydrogen peroxide in a liquid sample. The method may include measuring dissolved oxygen (DO) in the liquid sample, treating the sample with a catalyst, measuring the dissolved oxygen concentration of the treated sample, and calculating the difference in dissolved oxygen concentration between the two samples. The change in dissolved oxygen concentration may be used to determine the concentration of hydrogen peroxide in the sample. The increase in dissolved oxygen attributed to the catalytic destruction of hydrogen peroxide follows the equation:

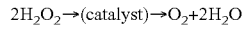

$$2H_2O_2 \rightarrow (catalyst) \rightarrow O_2 + 2H_2O$$

It has been recognized, however, that where the sample contains a high background concentration of dissolved oxygen, a comparatively low concentration of hydrogen peroxide may be difficult to detect by catalyst. For instance, the difference between the dissolved oxygen and hydrogen peroxide concentration in the sample may be outside the accuracy or resolution of a dissolved oxygen analyzer. In one example, raw water to be tested may have a concentration of dissolved oxygen of about 9000 ppb. The sample may have a concentration of hydrogen peroxide of about 2 ppb, equivalent to 0.94 ppb dissolved oxygen after catalytic treatment. The difference between the two concentrations in the example is 0.01% of the raw water sample. It may be difficult to detect such a low difference between the raw sample and the catalyst treated sample.

The systems and methods disclosed herein may be used to measure composition of an aqueous solution. In particular, the systems and methods may be used to measure composition of an aqueous solution having a high background concentration of dissolved oxygen. For instance, the systems and methods disclosed herein may be used to measure hydrogen peroxide concentration of the aqueous solution.

In accordance with one aspect, there is provided a method of determining composition of an aqueous solution. The aqueous solution may generally comprise hydrogen peroxide and dissolved oxygen. The method may comprise obtaining the aqueous solution from a source described herein. For instance, the source of the aqueous solution may be associated with a water purification, nuclear power generation, microelectronics manufacturing, semiconductor manufacturing, food processing, textile manufacturing, paper manufacturing and recycling, pharmaceutical manufacturing, chemical processing, and metal extraction system or process. The source of the aqueous solution may be associated with industrial applications, for example, with the removal of recalcitrant organic contaminants from industrial wastewaters. The source of the aqueous solution may be associated with wastewater and/or municipal water treatment. The source of the aqueous solution may be associated with an activated sludge water treatment system or method. In general, the aqueous solution may be associated with systems or methods for the removal of TOC from process waters.

In one particular embodiment, the source of the aqueous solution may be associated with a microelectronics manufacturing system or process. The source of the aqueous solution may be associated with a semiconductor manufacturing system or process. For instance, the aqueous solution may be a solution used for semiconductor chip or wafer manufacturing. In certain instances the disclosure may refer to semiconductor manufacturing systems. However, it should be noted that the systems and methods disclosed herein may similarly be employed in association with any aqueous solution for which accurate detection and/or careful control of hydrogen peroxide may be appropriate or necessary.

In general, the aqueous solution may be or comprise deionized water, ultrapure water, high purity water, distilled water, microfiltered water, ultrafiltered water, water that has been subjected to reverse osmosis, granular activated carbon treated water, or water that has otherwise been processed to remove contaminants. The aqueous solution may be associated with a system to produce high purity water, for example, deionized water, ultrapure water, distilled water, microfiltered water, ultrafiltered water, water that has been subjected to reverse osmosis, granular activated carbon treated water, or water that has otherwise been processed to remove contaminants. In some embodiments, the aqueous solution may comprise water that has been subjected to ultraviolet oxidation. In certain embodiments, the aqueous solution may comprise ultrapure water or be associated with a process to produce ultrapure water. As disclosed herein, ultrapure water may be defined by a resistivity at 25° C. of 18.18 MΩ·cm. Ultrapure water may have a TOC concentration of less than 10 ppb, for example, about 1 ppb or less. High purity water may be defined by a resistivity at 25° C. of between about 10 MΩ·cm and 18.18 MΩ·cm, for example, between about 10 MΩ·cm and 18 MΩ·cm. High purity water may have a TOC concentration of less than 100 ppb, for example, about 10 ppb or less, about 5 ppb or less, or about 2 ppb or less.

In certain embodiments, a sample portion of the aqueous solution may be obtained or extracted for testing. Thus, methods may comprise withdrawing a test sample from the aqueous solution. In other embodiments, a bulk of the aqueous solution may be tested. The aqueous solution may be substantially homogenous. For instance, any sample obtained from the aqueous solution may have substantially similar properties as the bulk of the aqueous solution. Such properties may include, for example, composition, temperature, viscosity, pH, and conductivity. In particular, any sample obtained from the aqueous solution may have a substantially similar composition as the bulk of the aqueous solution.

Systems and methods may comprise removing oxygen from the aqueous solution or from at least a portion of the aqueous solution, for example, from a test sample of the aqueous solution. Oxygen may be removed from the aqueous solution or sample by any method known to remove oxygen from an aqueous sample. In certain embodiments, removing oxygen from the aqueous solution or sample may comprise directing the solution or sample to an oxygen removal process. Non-limiting examples of oxygen removal systems and methods include vacuum degasification, gas transfer (for example, contact with a gas transfer membrane), oxygen scavenging (for example, contact with an oxygen scavenging media), and vacuum mechanical agitation. Other examples of oxygen removal methods include thermal degasification and sparging. Yet other example methods are within the scope of the disclosure.

The systems and methods may employ one or more of the oxygen removal methods disclosed herein. The oxygen removal system or process may be configured to remove at least 80% of the oxygen from the aqueous solution or sample. The oxygen removal may be configured to remove at least 90%, at least 95%, at least 99%, at least 99.9%, at least 99.99%, or 99.999%, of the oxygen in the aqueous solution or sample. In certain embodiments, more than one oxygen removal method may be employed to achieve a desired removal rate of oxygen.

Vacuum degasification may be performed in a specialized vacuum chamber, sometimes referred to as a vacuum degasser. Vacuum degasification generally involves pressure reduction to degas the aqueous solution. Briefly, the solubility of a gas in the aqueous solution obeys Henry's law. The amount of dissolved gas in the liquid is typically proportional to its partial pressures. Vacuum degasification generally involves placing the aqueous solution under reduced pressure to make the dissolved gas less soluble. During vacuum degasification the solution may be sonicated and/or stirred to enhance the efficiency of the degasification. Thus, the vacuum chamber may comprise a sonicator and/or stirrer.

Gas transfer with a gas transfer membrane is sometimes referred to as membrane degasification. Gas transfer generally involves contact with a membrane. The membrane may be configured to enable gas-liquid separation by being permeable to gasses and impermeable to liquids. For instance, flowing an aqueous solution inside a gas transfer membrane may selectively pass dissolved gas, leaving substantially pure solvents on the filtrate side. The membrane degasification may be performed under vacuum conditions. The membrane degasification may be performed with an inert sweep gas, such as nitrogen, argon, or helium. Any inert sweep gas may be employed. The membranes may also be configured to prevent redissolution of the gas into the liquid. One exemplary gas transfer membrane is the Liqui-Cel™ Membrane contactor (distributed by 3M™, Maplewood, MN).

Oxygen scavenging may generally involve contact with an oxygen scavenging media. The oxygen scavenging media may have a composition and packaging configured for removal of oxygen from an aqueous solution. In some embodiments, the oxygen scavenging media may also remove carbon dioxide. The oxygen scavenging media may be in liquid, solid, or gel form. In general, the oxygen scavenging media may be contained in an aqueous solution permeable packaging. The aqueous solution permeable packaging may be substantially impermeable to the oxygen scavenging media and any biproducts and broken-down components of the oxygen scavenging media. The aqueous solution permeable packaging may be inert to the aqueous solution. The oxygen scavenging media may be or comprise one or more of sulfite, bisulfite, carbohydrazide, tannin, and diethylhydroxylamine.

Vacuum mechanical agitation may generally involve mechanically agitating the aqueous solution under vacuum conditions to increase surface contact of the aqueous solution with a scrubbing atmosphere. The scrubbing atmosphere may include an inert gas, such as nitrogen, argon, or helium. The mechanical agitation may be performed by creating fine droplets or thin films of the aqueous solution. Mechanical agitation may include one or more of spraying, atomizing, and cascading. Thus, a mechanical agitation unit may comprise a vacuum spray unit, vacuum atomizer, or vacuum cascading tray. Mechanical agitation may be performed under temperature controlled conditions. Thus, the vacuum mechanical agitation unit may be temperature controlled.

Thermal degasification may generally include thermally treating the aqueous solution to expel dissolved gas. The thermal treatment may be heating or cooling, depending on the solvent and the gas. Typically, aqueous solutions expel gas at increased temperatures. Thus, thermal degasification of the aqueous solution may involve heating the aqueous solution. Thermal degasification may be performed in any temperature control unit. During thermal degasification the solution may be sonicated and/or stirred to enhance the efficiency of the degasification. Thus, the temperature control unit may comprise a sonicator and/or stirrer.

Sparging may typically involve bubbling an inert gas through the solution to pull out undesired dissolved gases. A sparger may be used to infuse fine bubbles into the aqueous solution. The inert gas may be one that has a low solubility or substantially no solubility in the aqueous solution at the sparging conditions (for example, at the sparging temperature and pressure). The inert gas may have a controlled composition and/or be substantially pure. Exemplary inert gases include nitrogen, argon, and helium. Other inert gases may be employed. During sparging, the solution is typically stirred vigorously to enhance the efficiency of the degasification. Thus, the sparger may include a stirrer.

Reducing agents may be used to remove oxygen from the aqueous solution. In some embodiments, any additives put in contact with the aqueous solution are inert. In other embodiments, any additives put in contact with the aqueous solution are non-soluble. Non-soluble and/or inert additives may be contained in a packaging or vessel to prevent distribution in the aqueous solution. Effluent from the aqueous solution composition analysis systems and methods described herein may generally be substantially free of reactive additives and compounds. Effluent from the aqueous solution composition analysis systems and methods described herein may generally be substantially free of composition analysis additives.

Systems and methods may comprise determining a concentration of dissolved oxygen in the aqueous solution or sample. The solution or sample may be subjected to dissolved oxygen monitoring before an oxygen removal process. The solution or sample may be subjected to dissolved oxygen monitoring after an oxygen removal process. The dissolved oxygen concentration of the aqueous solution or sample may be determined by any method known to measure dissolved oxygen concentration of an aqueous solution. In a particular embodiment, the concentration of dissolved oxygen may be determined by use of a dissolved oxygen analyzer. In certain embodiments, the concentration of dissolved oxygen may be determined by use of a plurality of dissolved oxygen analyzers. For example, 1-5 or 2-5 dissolved oxygen analyzers may be used to determine dissolved oxygen concentration of the aqueous solution or sample.

The dissolved oxygen analyzer may generally include one or more liquid phase dissolved oxygen meters. In general, measurement of the dissolved oxygen may be performed with a measurement cell. The sample stream may flow through the measurement cell contacting a semi-permeable membrane which detects oxygen through an electrochemical process in the form of an electrochemical signal. The analyzer may convert the electrical signal into a concentration of dissolved oxygen. The analyzer may be configured to accept electrical signals from several measurement cells and analyze and/or report the dissolved oxygen concentration for each of the measurement cells. The analyzer may report an average dissolved oxygen concentration from each of the measurements obtained from the measurement cells.

The dissolved oxygen analyzer may be configured for in-line measurement of dissolved oxygen in the aqueous solution. The dissolved oxygen analyzer may be calibrated to measure dissolved oxygen content of between about 10 ppm and 1 ppb. In some embodiments, a dissolved oxygen analyzer positioned upstream from an oxygen removal process may be calibrated to measure dissolved oxygen content of between about 10 ppm and 1 ppm. A dissolved oxygen analyzer positioned downstream from an oxygen removal process may be calibrated to measure dissolved oxygen content of between about 100 ppb and about 1 ppb.

Systems and methods may comprise determining a concentration of other dissolved gases in the aqueous solution or sample. Such dissolved gases include, for example, nitrogen and carbon dioxide. In some embodiments, the dissolved oxygen analyzer may be configured to measure concentration of the other dissolved gases. Alternatively, additional dissolved gas analyzers may be employed and included in the system.

The method may comprise removing hydrogen peroxide from at least a portion of the aqueous solution or sample. In general, the hydrogen peroxide may be removed from a solution or sample which has previously been subjected to oxygen removal. In certain instances, for example, where dissolved oxygen concentration of the aqueous solution is below a predetermined threshold, hydrogen peroxide may be removed from a solution or sample which has not been subjected to oxygen removal. In general, the hydrogen peroxide may be removed from a solution or sample which has been analyzed for dissolved oxygen concentration.

Hydrogen peroxide may be removed by a hydrogen peroxide destruction process or system. Thus, in certain embodiments, removing hydrogen peroxide from the solution or sample may comprise directing the solution or sample to a hydrogen peroxide destruction process or system. The hydrogen peroxide destruction process or system may be configured to remove at least 80% of the hydrogen peroxide. The hydrogen peroxide destruction process or system may be configured to remove at least 90%, at least 95%, at least 99%, at least 99.9%, at least 99.99%, or 99.999%, of the hydrogen peroxide in the aqueous solution or sample. In certain embodiments, more than one hydrogen peroxide destruction process or system may be employed to achieve a desired removal rate of hydrogen peroxide.

The hydrogen peroxide destruction system or process may generally involve a catalyst-driven hydrogen peroxide destruction method. The catalyst-driven hydrogen peroxide method may involve contact with a heterogeneous catalyst or a homogeneous catalyst. For instance, the methods may comprise directing the solution or sample to a vessel comprising a hydrogen peroxide destruction catalyst. Non-limiting examples of catalyst-driven hydrogen peroxide destruction methods include, for example, contact with ion exchange resin, contact with a metal, and contact with an enzyme. Other exemplary methods include treatment with granular activated carbon and treatment with sodium sulfite. The vessel may comprise one or more of the hydrogen peroxide destruction catalysts described herein.

Contact with a hydrogen peroxide destruction ion exchange resin may generally involve directing the solution or sample to a vessel comprising the ion exchange resin. The ion exchange resin may include anion exchange resin, cation exchange resin, and mixed-bed resin. The ion exchange resin may be doped with a hydrogen peroxide destruction metal. In a particular embodiment, the ion exchange resin may be or include metal-doped anion exchange resin. The ion exchange resin may be or include palladium-doped anion exchange resin.

The hydrogen peroxide destruction metal may be immobilized on a substrate or the ion exchange resin. Thus, in certain embodiments, contact with a hydrogen peroxide destruction metal may generally involve directing the solution or sample to a vessel comprising the hydrogen peroxide destruction metal immobilized on a substrate. The hydrogen peroxide destruction metal may comprise a metal from the group of noble metals. The hydrogen peroxide destruction metal may be or comprise palladium, platinum, titanium, ruthenium, osmium, iridium, or rhodium. The hydrogen peroxide destruction metal may be or comprise zinc, gold, or silver. The hydrogen peroxide destruction metal may be or comprise mercury, rhenium, or copper. The substrate may comprise an inert material. Exemplary inert materials include silicon and silicon compounds. Other inert materials may be employed. The substrate may be or comprise an ion exchange resin, a polymer material, or a ceramic material.

In certain embodiments, the hydrogen peroxide destruction method may comprise directing the solution or sample to a vessel comprising an enzyme. The enzyme may be free-flowing in the vessel. The enzyme may be contained in an inert packaging. The inert packaging may be permeable to the aqueous solution or sample. In other embodiments, the enzyme may be immobilized on a substrate. One non-limiting example of a hydrogen peroxide destruction enzyme is catalase. Any hydrogen peroxide destruction enzyme may be employed.

The method may further comprise determining the concentration of dissolved oxygen in a sample which has been treated for removal of hydrogen peroxide, as previously described. The sample may be one that was analyzed for dissolved oxygen concentration prior to removal of hydrogen peroxide. Determining the concentration of dissolved oxygen in the sample may comprise directing the sample to a dissolved oxygen analyzer, as previously described. The methods may additionally or alternatively comprise determining a concentration of another dissolved gas in the sample, as previously described.

To determine the concentration of hydrogen peroxide in the aqueous solution, the method may comprise performing one or more calculations to determine a relationship between the dissolved oxygen concentration of the solution or a sample prior to removal of hydrogen peroxide and the dissolved oxygen concentration of the solution or sample after removal of the hydrogen peroxide. The relationship may be a difference between the dissolved oxygen concentration of the two samples. In general, the relationship may be a stoichiometric difference. The relationship is defined by the chemical equation:

$$2H_2O_2 \rightarrow O_2 + 2H_2O$$

Thus, the calculation may involve multiplying the difference in dissolved oxygen concentration of the samples by 2.125 to determine the concentration of hydrogen peroxide in the aqueous solution or sample prior to performing the analytical methods described herein. The calculated hydrogen peroxide concentration may be the substantially equivalent to the hydrogen peroxide concentration of the bulk aqueous solution.

In certain embodiments, for example, where the concentration of hydrogen peroxide is greater than about 2 ppb, the method may further comprise treating at least a portion of the aqueous solution or sample for removal of hydrogen peroxide. The hydrogen peroxide may be removed by any of the hydrogen peroxide removal methods described herein. The hydrogen peroxide may be removed to produce a treated solution having less than about 2 ppb of hydrogen peroxide. The methods may comprise delivering the treated solution to a point of use. Thus, in certain embodiments, the systems may be fluidly connectable or fluidly connected to a point of use.

The point of use may include, for example, water purification, nuclear power generation, microelectronics manufacturing, semiconductor manufacturing, food processing, textile manufacturing, paper manufacturing and recycling, pharmaceutical manufacturing, chemical processing, or a metal extraction system or process. In a particular embodiment, the point of use may include a microelectronics manufacturing or semiconductor manufacturing system or process. In certain embodiments, the treated solution may be post-treated before delivery to the point of use. Thus, in certain embodiments, the systems may be fluidly connectable or fluidly connected to a post-treatment unit.

In certain embodiments, one or more parameters of the aqueous solution and/or product solution may be considered. For example, one or more of flow rate, pH, temperature, and conductivity may be considered. The methods may include subjecting the aqueous solution to the methods of detecting composition described herein responsive to a measurement of one or more parameter being outside tolerance of a target value. The methods may include treating the aqueous solution for removal of oxygen and/or hydrogen peroxide responsive to a measurement of the one or more parameter.

In accordance with some embodiments, a first sample of the aqueous solution may be subjected to oxygen removal. The concentration of dissolved oxygen may be measured for the first sample after oxygen removal. A second sample of the aqueous solution may be subjected to oxygen removal and hydrogen peroxide destruction. The concentration of dissolved oxygen of the second sample may be measured after oxygen removal and hydrogen peroxide destruction. The difference in dissolved oxygen concentration of the samples may be used to calculate the hydrogen peroxide concentration of the aqueous solution. Thus, the hydrogen peroxide concentration may be determined by analysis of more than one sample of the aqueous solution. Such a method may be used when retrofitting an existing system. This exemplary method may be performed with a single dissolved oxygen analyzer.

Systems for determining composition of an aqueous solution are disclosed herein. As shown in FIG. 1A, an exemplary system 10 may comprise a feed line 102 fluidly connectable to a source of the aqueous solution 100. The source of the aqueous solution 100 may comprise a concentration of hydrogen peroxide and a concentration of dissolved oxygen. The system 10 may comprise an oxygen removal unit 200 having an inlet fluidly connected to the feed line 102. The system may comprise a dissolved oxygen analyzer 500 having an inlet fluidly connected to the oxygen removal unit 200 via valve 420. The system 10 may comprise a hydrogen peroxide removal unit 400 having an inlet fluidly connected to oxygen removal unit 200. Hydrogen peroxide removal unit 400 may be fluidly connected to dissolved oxygen analyzer 500 via valve 422.

Figure 1B:
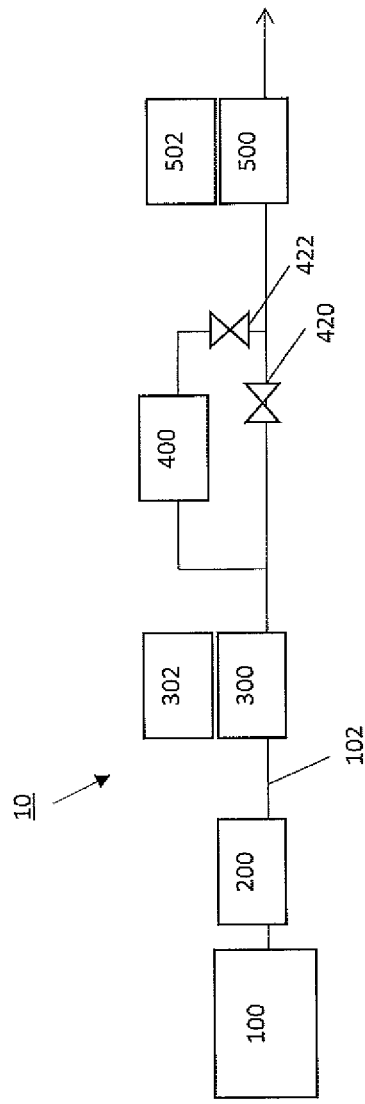
FIG. 1B is a box diagram of a system for determining hydrogen peroxide concentration of an aqueous solution, according to one embodiment.

As shown in FIG. 1B, the system 10 may comprise a second dissolved oxygen analyzer 300 having an inlet fluidly connected to the oxygen removal unit 200. The hydrogen peroxide removal unit 400 may have an inlet fluidly connected to the second dissolved oxygen analyzer 300. Thus, the system may comprise one or more dissolved oxygen analyzers. A single dissolved oxygen analyzer may provide accurate results for comparison of dissolved oxygen concentration between a sample which has been treated for hydrogen peroxide destruction and one which has not been treated. However, multiple dissolved oxygen analyzers may be calibrated for accurate results. Regular and periodic calibrations of the multiple dissolved oxygen analyzers may be performed.

The first dissolved oxygen analyzer 500 and the second dissolved oxygen analyzer 300 may each comprise a display unit 502, 302 respectively (shown in FIGS. 1A and 1B). The display units 502, 302 may be configured to display dissolved oxygen concentration in the solution or sample.

Figure 3:
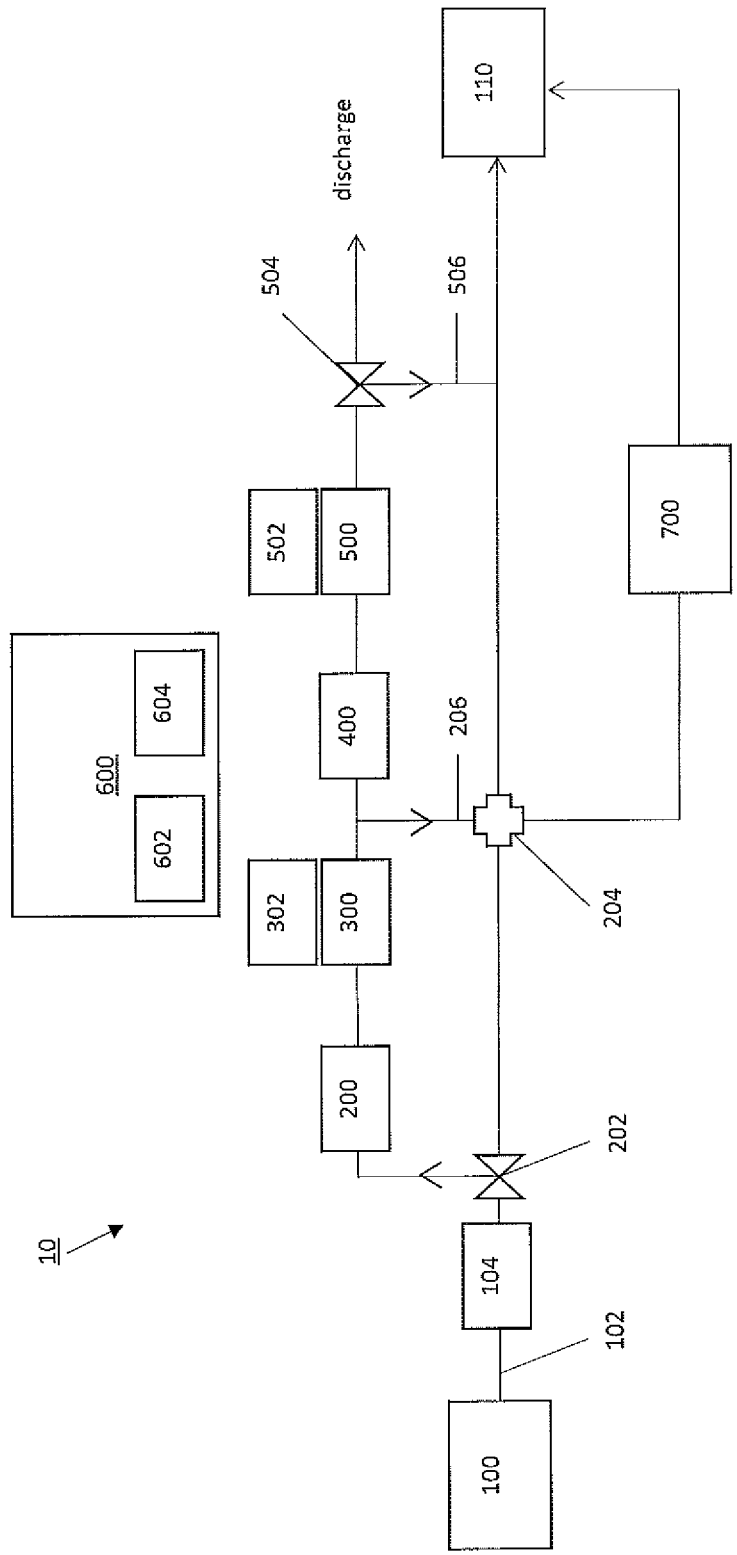
FIG. 3 is a schematic diagram of a system for determining hydrogen peroxide concentration of an aqueous solution, according to one embodiment.

As shown in FIG. 3, the system may comprise a control module 600 electrically connected to the dissolved oxygen analyzer 300 and the dissolved oxygen analyzer 500. The control module 600 may be configured to calculate a difference between a concentration of dissolved oxygen measured prior to hydrogen peroxide destruction and dissolved oxygen measured after hydrogen peroxide destruction. In a system containing more than one dissolved oxygen analyzer (as shown in FIG. 3) the control module 600 may calculate the difference between a concentration measured by the first dissolved oxygen analyzer 500 and a concentration of dissolved oxygen measured by the second dissolved oxygen analyzer 300. The difference may be used to determine the concentration of hydrogen peroxide in the aqueous solution 100, as previously described.

The control module 600 may be capable of determining the concentration of hydrogen peroxide of about 20 ppb or less. For instance, the control module 600 may be capable of determining the concentration of hydrogen peroxide of about 10 ppb or less, about 8 ppb or less, about 6 ppb or less, about 5 ppb or less, about 4 ppb or less, about 2 ppb or less, or about 1 ppb or less.

The control module 600 may be or comprise any electronic or computing device known to one of ordinary skill in the art. The control module may include input devices, for example, a touch pad, a touch screen, a key pad, a keyboard, a microphone, and/or a mouse. The control module may include output devices, for example, a screen, a light (for example, an LED light), and/or a speaker. The control module may be electrically or operatively connected to the one or more components via a wire or wireless connection. The control module and each of the components may be electrically or operatively connected via an internet connection, for example, a Wi-Fi, or Bluetooth connection. Optionally, the connection may be made to a server or directly between components. The control module may be electrically connected to a power source.

The control module 600 may have a display unit 602 configured to display measured and/or calculated concentrations of dissolved oxygen and/or hydrogen peroxide.

The control module 600 may be coupled with one or more memory storing unit 604. For example, the control module 600 may include one or more processors typically connected to the memory storing unit 604, which can comprise, for example, any one or more of a disk drive memory, a flash memory device, a RAM memory device, or other device for storing data. Memory storing unit 604 may be used for storing programs and data during operation of the system 10 and/or control module 600. For example, memory storing unit 604 may be used for storing historical data relating to the parameters over a period of time, as well as operating data. Software, including programming code that implements embodiments, can be stored on a computer readable and/or writeable nonvolatile recording medium, and then typically copied into memory device 604 wherein it can then be executed by one or more processor of the control module 600. Such programming code may be written in any of a plurality of programming languages, for example, Java, Visual Basic, C, C#, or C++, Fortran, Pascal, Eiffel, Basic, COBAL, or any of a variety of combinations thereof.

In certain embodiments, at least one of the source of the aqueous solution 100 and the oxygen removal unit 200 may be fluidly connectable to a water treatment subsystem 700 (shown in FIG. 3 fluidly connectable to the source of the aqueous solution 100). The control module 600 may be configured to deliver at least one of the aqueous solution 100 and an oxygen removal unit 200 effluent to the water treatment subsystem 700 responsive to the concentration of hydrogen peroxide being determined to be greater than about 10 ppb. In some embodiments, the control module 600 may be configured to deliver at least one of the aqueous solution 100 and an oxygen removal unit 200 effluent to the water treatment subsystem 700 responsive to the concentration of hydrogen peroxide being determined to be greater than about 5 ppb, or greater than about 2 ppb. The control module 600 may deliver the aqueous solution 100 or the oxygen removal unit 200 effluent by actuation of valve 202. Additional or alternative valves may be positioned on feed line 102 and/or on effluent line 206.

In certain embodiments, at least one of the source of the aqueous solution 100 and the oxygen removal unit 200 may be fluidly connectable to a point of use 110 (shown in FIG. 3 fluidly connectable to the source of the aqueous solution 100). The control module 600 may be configured to deliver at least one of the aqueous solution 100 and an oxygen removal unit 200 effluent to the point of use 110 responsive to the concentration of hydrogen peroxide being determined to be about 10 ppb or less. In certain embodiments, the control module 600 may be configured to deliver at least one of the aqueous solution 100 and an oxygen removal unit 200 effluent to the point of use 110 responsive to the concentration of the hydrogen peroxide being determined to be about 5 ppb or less or about 2 ppb or less. The control module 600 may deliver the aqueous solution 100 by actuation of valve 202, shown on feed line 102. The control module 600 may deliver the oxygen removal unit 200 effluent by actuation of valve 204, shown on effluent line 206.

In certain embodiments, the water treatment subsystem 700 may be fluidly connectable to a point of use 110. In particular embodiments, the point of use 110 may be a semiconductor manufacturing subsystem.

In certain embodiments, the feed line 102 may comprise an inlet fluidly connected to the second dissolved oxygen analyzer 500 downstream from the oxygen removal unit 200, shown in FIG. 3 as effluent line 506. The control module 600 may be configured to actuate valve 504 to deliver dissolved oxygen analyzer 500 effluent to feed line 102, and downstream, to point of use 110. In some embodiments, the control module 600 may be configured to deliver the dissolved oxygen analyzer 500 effluent to feed line 102 responsive to the responsive to the concentration of hydrogen peroxide being determined to be about 10 ppb or less. In certain embodiments, the control module 600 may be configured to deliver the dissolved oxygen analyzer 500 effluent to feed line 102 responsive to the concentration of the hydrogen peroxide being determined to be about 5 ppb or less or about 2 ppb or less. In other embodiments, the control module 600 may be configured to deliver the dissolved oxygen analyzer 500 effluent to a discharge.

The system may comprise a dissolved oxygen analyzer 104 positioned upstream from the oxygen removal unit 200. Dissolved oxygen analyzer 104 may be configured to determine concentration of dissolved oxygen in the source of the aqueous solution 100 prior to the oxygen removal unit 200. Dissolved oxygen analyzer 104 may be electrically connected to a flow controller which may be associated with control module 600 or independent from control module 600 (in FIG. 3, the flow controller is shown as control module 600). The flow controller may be programmed to notify a user responsive to the dissolved oxygen analyzer 104 measuring a concentration of dissolved oxygen in the aqueous solution or sample greater than the threshold concentration. The flow controller may be programmed to direct the aqueous solution or a sample of the aqueous solution to the oxygen removal unit 200 responsive to the dissolved oxygen analyzer 104 measuring a concentration of dissolved oxygen in the aqueous solution or sample greater than the threshold concentration. The flow controller may be configured to actuate the delivery of the aqueous solution or a sample to the oxygen removal unit 200 via valve 202 positioned on the feed line 102, upstream from the oxygen removal unit 200.

In certain embodiments, the threshold value may be about 500 ppb of dissolved oxygen. The threshold value may be about 1 ppm of dissolved oxygen. The threshold value may be about 2 ppm, about 3 ppm, about 4 ppm, about 5 ppm, about 6 ppm, about 7 ppm, about 8 ppm, about 9 ppm, or about 10 ppm of dissolved oxygen. Thus, the flow controller may be configured to notify a user and/or actuate valve 202 to initiate the treatments and measurements for determining concentration of hydrogen peroxide in the aqueous solution. Responsive to the calculated concentration of hydrogen peroxide, the control module 600 may actuate valve 204 to initiate treatment of the aqueous solution prior to being delivered to point of use 110.

Figure 2:
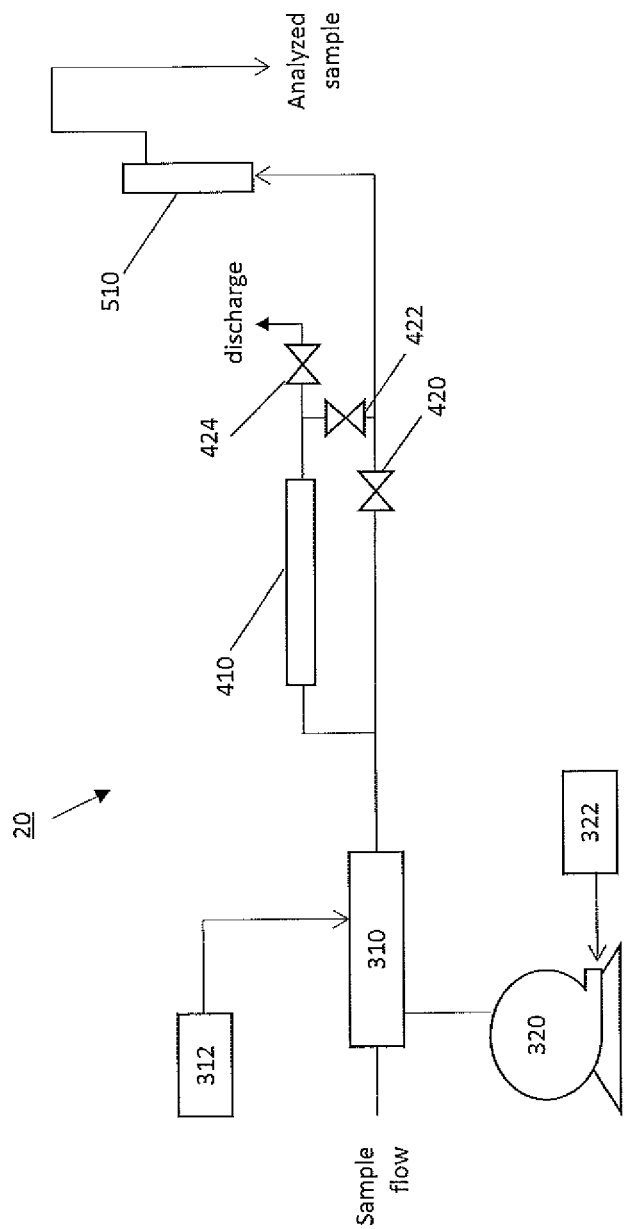
FIG. 2 is a box diagram of a system for determining hydrogen peroxide concentration of an aqueous solution, according to one embodiment.

FIG. 2 is a schematic diagram of an exemplary system 20 for determining concentration of hydrogen peroxide in an aqueous sample. System 20 may be provided to retrofit an existing aqueous solution system. In particular, a sample of the aqueous solution may be directed to system 20 for analysis. System 20 includes gas transfer membrane 310 which is operated as a vacuum membrane degasifier by vacuum pump 320 supplied with chilled water supply 322. A source of an inert gas 312 is in fluid communication with gas transfer membrane 310. System 20 further includes catalytic hydrogen peroxide destruction column 410 in a parallel line actuated by valves 420 and 422. System 20 includes valve 424 positioned downstream from hydrogen peroxide destruction column 410. Valve 424 may be configured to direct the aqueous solution to discharge when valve 422 is closed. Valve 424 may be provided to ensure continuous flow of solution through hydrogen peroxide destruction column 410. Continual flow through the hydrogen peroxide destruction column 410 may provide faster measurements, for example, by avoiding a need to re-calibrate the column. System 20 further includes dissolved oxygen analyzer 510.

In certain embodiments, for example, as shown in the system of FIG. 2, a single dissolved oxygen analyzer 510 may be used to determine the concentration of hydrogen peroxide in the aqueous solution. The catalyst for destruction of hydrogen peroxide 410 may be arranged on a parallel arm of the solution or sample line. The system 20 may include one or more valves 420, 422 to direct water to the hydrogen peroxide destruction catalyst 410 or directly to the dissolved oxygen analyzer 510. In a first mode of operation, the system may be configured such that the solution or sample may bypass the hydrogen peroxide destruction catalyst 410 and be directed to the dissolved oxygen analyzer 510 (valve 420 is open and valve 422 is closed). In a second mode of operation, the system may be configured such that the solution or sample may be directed to the hydrogen peroxide destruction catalyst 410 upstream from the dissolved oxygen analyzer 510 (valve 420 is closed and valve 422 is open). The difference between the measured dissolved oxygen concentration in the second mode of operation and the first mode of operation may be used to calculate the hydrogen peroxide concentration.

Figure 4A:
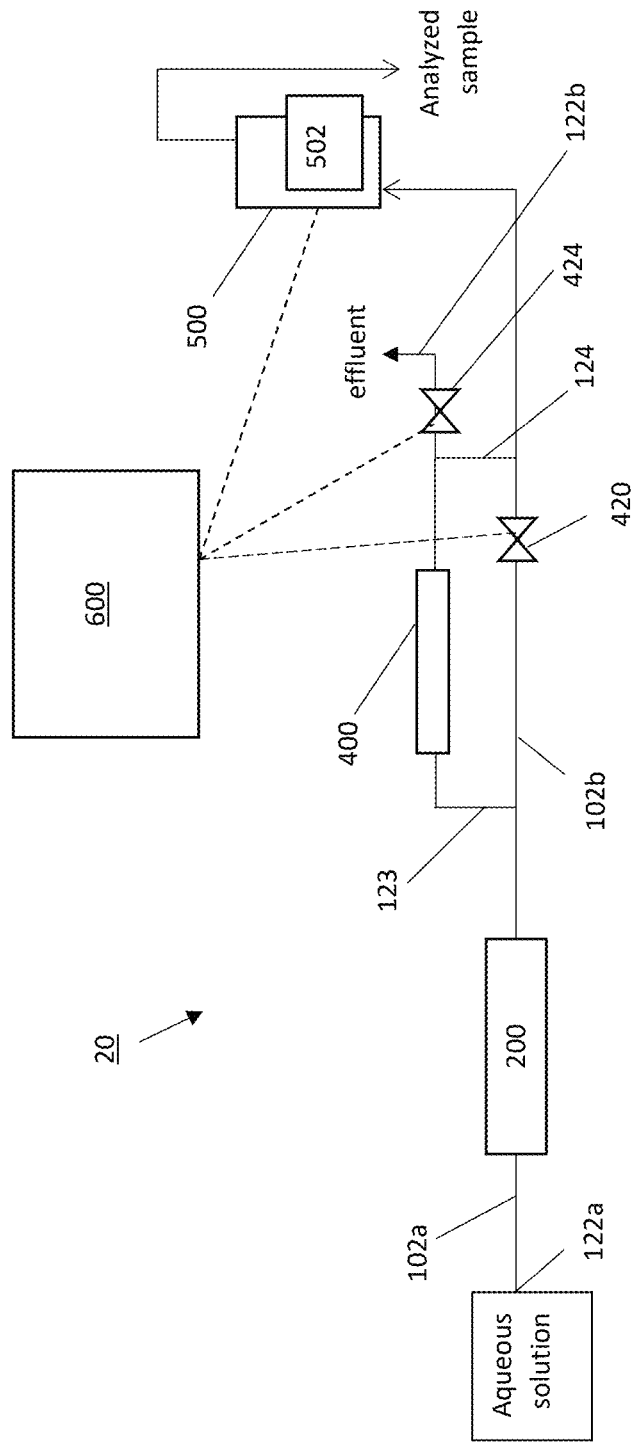
FIG. 4A is a box diagram of a system for determining composition of an aqueous solution, according to one embodiment.

FIG. 4A is a box diagram of a system for determining composition of an aqueous solution, according to one embodiment. The exemplary system 20 of FIG. 4A includes feed line 102a, 102b having a feed inlet 122a fluidly connectable to a source of the aqueous solution, oxygen removal unit 200 fluidly connected to feed line 102a, 102b, and dissolved oxygen analyzer 500 having display unit 502 fluidly connected to feed line 102a, 102b downstream from the dissolved oxygen analyzer 200. Exemplary system 20 includes first conduit 123 fluidly connected to feed line 102a, 102b between the oxygen removal unit 200 and dissolved oxygen analyzer 500, hydrogen peroxide removal unit 400 fluidly connected to the first conduit 123 downstream from the oxygen removal unit 200. The first conduit 123 fluidly connects the feed inlet 122a to effluent outlet 122b on the first conduit 123 downstream from the hydrogen peroxide removal unit 400. Exemplary system 20 includes second conduit 124 fluidly connected to first conduit 123 between the hydrogen peroxide removal unit 400 and effluent outlet 122b. Second conduit 124 extends back to feed line 120b and fluidly connects the hydrogen peroxide removal unit 400 to the dissolved oxygen analyzer 500. Exemplary system 20 includes a first valve 424 positioned on the first conduit 123 between the hydrogen peroxide removal unit 400 and the effluent outlet 122b and a second valve 420 positioned on the feed line 120b between the oxygen removal unit 200 and the dissolved oxygen analyzer 500. Exemplary system 20 includes control module 600 connected to the first valve 424, the second valve 420 and the dissolved oxygen analyzer 500.

Figure 4B:
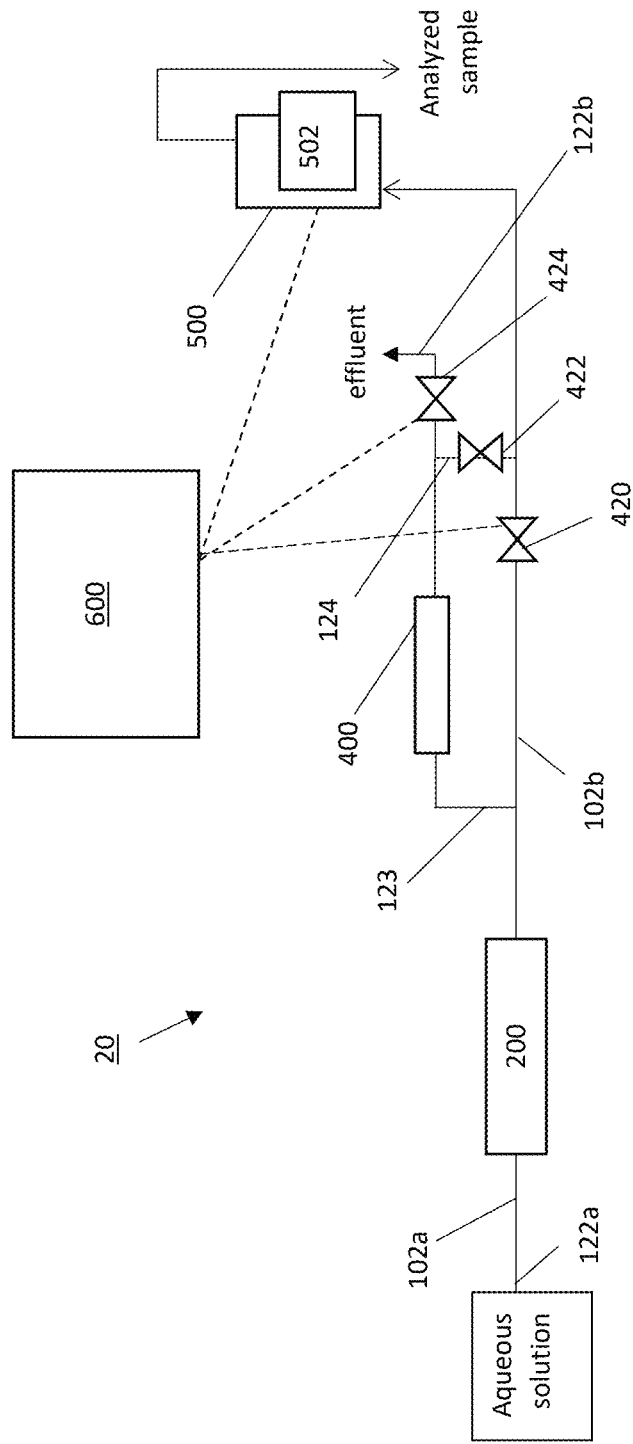
FIG. 4B is a box diagram of a system for determining composition of an aqueous solution, according to one embodiment.

FIG. 4B is a box diagram of a system for determining composition of an aqueous solution, according to one embodiment. Exemplary system 20 of FIG. 4B is similar to system 20 of FIG. 4A, except that it further includes a third valve 422 positioned on the second conduit 124 between the hydrogen peroxide removal unit 400 and the dissolved oxygen analyzer 500.

Figure 5A:
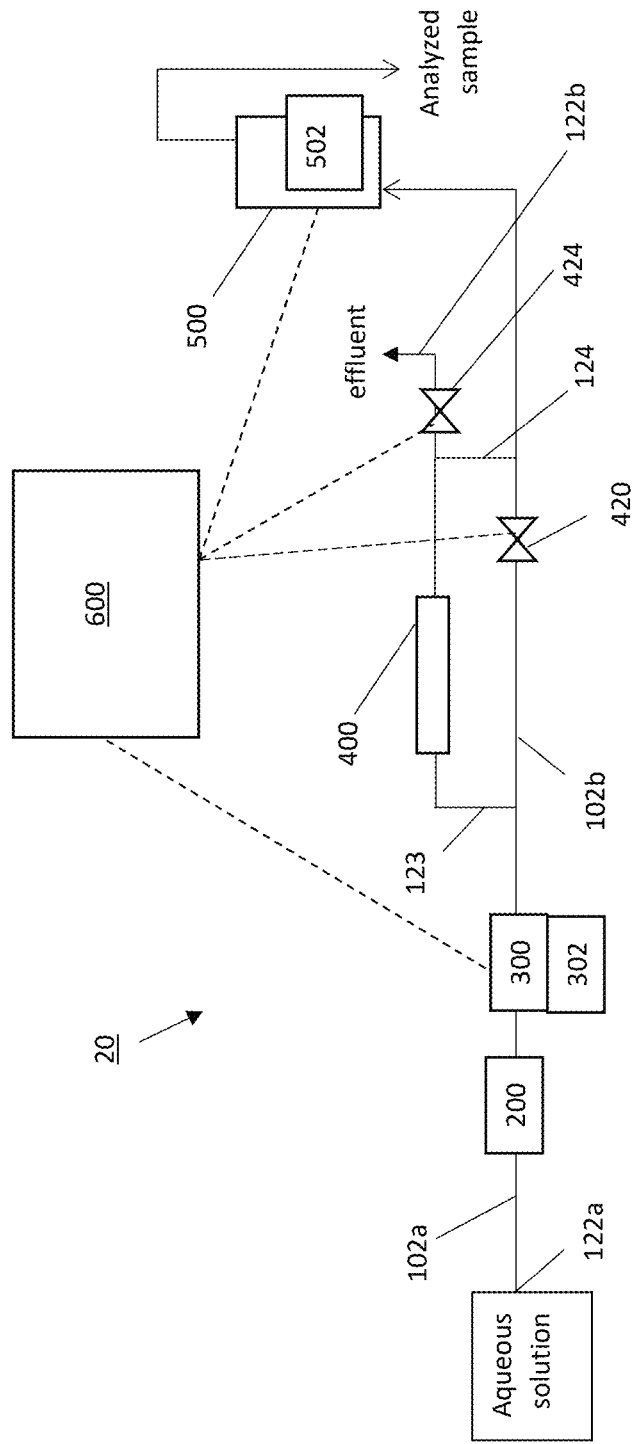
FIG. 5A is a box diagram of a system for determining composition of an aqueous solution, according to one embodiment.

FIG. 5A is a box diagram of a system for determining composition of an aqueous solution, according to one embodiment. Exemplary system 20 of FIG. 5A includes feed line 102a, 102b having a feed inlet 122a fluidly connectable to a source of the aqueous solution, oxygen removal unit 200 fluidly connected to feed line 102a, 102b, and second dissolved oxygen analyzer 300 having display unit 302 fluidly connected to feed line 102a, 102b downstream from the dissolved oxygen analyzer 200. Feed line 102a, 102b may fluidly connect feed inlet 122a to the second dissolved oxygen analyzer 300. Exemplary system 20 includes first conduit 123 fluidly connected to feed line 102a, 102b downstream from the oxygen removal unit 200 and hydrogen peroxide removal unit 400 fluidly connected to the first conduit 123 downstream from the oxygen removal unit 200. The first conduit 123 fluidly connects the feed inlet 122a to effluent outlet 122b on the first conduit 123 downstream from the hydrogen peroxide removal unit 400. Exemplary system 20 includes a first dissolved oxygen analyzer 500 having display unit 502 fluidly connected to the first conduit 123 downstream from the hydrogen peroxide removal unit 400.

Exemplary system 20 includes second conduit 124 fluidly connected to first conduit 123 between the hydrogen peroxide removal unit 400 and effluent outlet 122b. Second conduit 124 extends back to feed line 120b and fluidly connects the hydrogen peroxide removal unit 400 to the first dissolved oxygen analyzer 500. Exemplary system 20 includes a first valve 424 positioned on the first conduit 123 between the hydrogen peroxide removal unit 400 and the effluent outlet 122b and a second valve 420 positioned on the feed line 120b downstream from the oxygen removal unit 200 and the second dissolved oxygen analyzer 300. Exemplary system 20 includes control module 600 connected to the first valve 424, the second valve 420, the second dissolved oxygen analyzer 300, and the first dissolved oxygen analyzer 500.

Figure 5B:
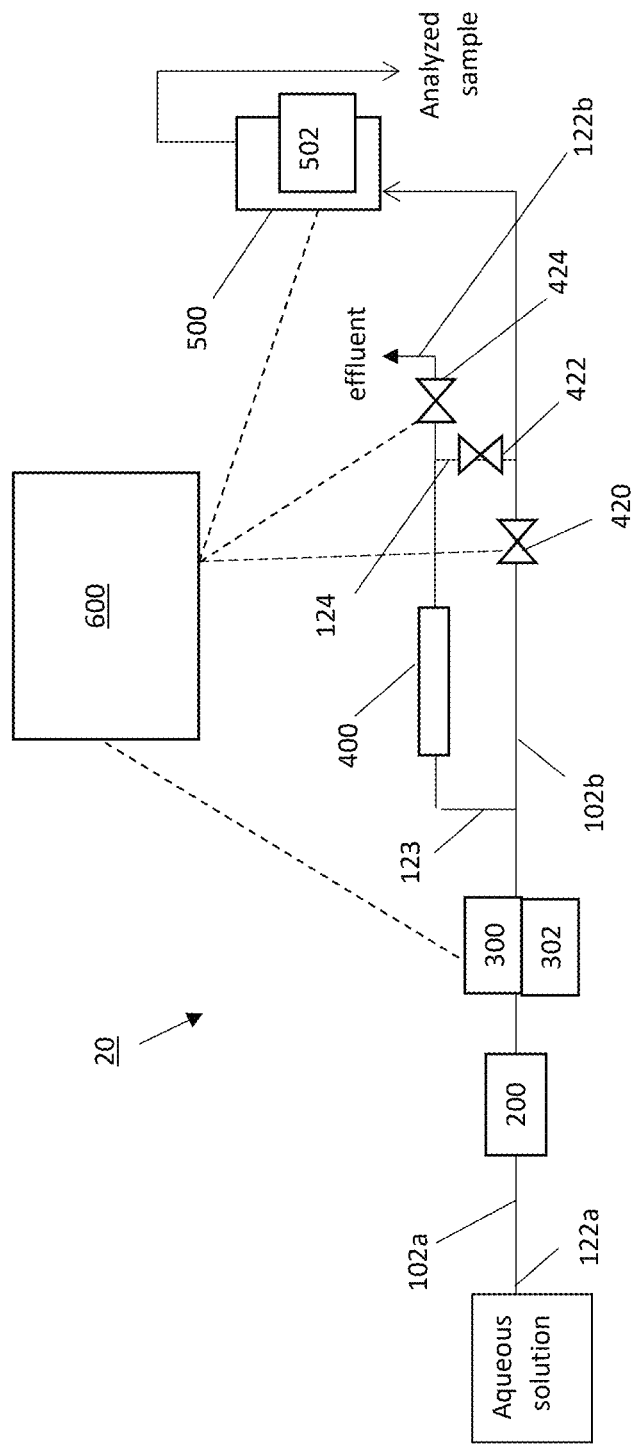
FIG. 5B is a box diagram of a system for determining composition of an aqueous solution, according to one embodiment.

FIG. 5B is a box diagram of a system for determining composition of an aqueous solution, according to one embodiment. Exemplary system 20 of FIG. 5B is similar to system 20 of FIG. 5A, except that it further includes a third valve 422 positioned on the second conduit 124 between the hydrogen peroxide removal unit 400 and the first dissolved oxygen analyzer 500.

Methods of facilitating the measurement of hydrogen peroxide concentration in an aqueous solution are also disclosed herein. The methods may include providing a system for determining the composition of an aqueous solution, as previously described. The methods may include providing any one or more component of the system described herein, for example, to facilitate retrofitting of an existing aqueous solution system. One exemplary component that may be provided is the control module. In some embodiments, a programming control scheme may be provided for programming an existing control module. In other embodiments, a flow controller may be provided which operates independently from an existing control module. One or more sensors, pumps, and valves may be provided to retrofit an existing system. Exemplary sensors that may be included in the system include flow meters, pH meters, thermometers, and conductivity meters. The control module may be programmed or configured to consider one or more measurements obtained by the sensors and instruct the system responsive to the one or more obtained measurements. The methods may comprise providing instructions to install and/or interconnect the one or more components provided, as described above.

The methods disclosed herein may additionally include providing instructions for determining composition of the aqueous solution. The methods may include instructing a user to perform any of the steps described herein. For instance, the methods may include instructing a user to take a sample of the aqueous solution. The methods may include instructing a user to remove oxygen from the aqueous solution or sample. The methods may include instructing a user to determine dissolved oxygen concentration of the aqueous solution or sample. The methods may include instructing a user to destroy hydrogen peroxide in the aqueous solution or sample. The methods may include instructing a user to determine dissolved oxygen concentration of the aqueous solution or sample after destruction of hydrogen peroxide. The methods may include instructing a user to calculate the hydrogen peroxide concentration by determining the difference between the dissolved oxygen concentration after hydrogen peroxide destruction and before hydrogen peroxide destruction. The methods may additionally include instructing a user to treat the aqueous solution responsive to the calculation of the hydrogen peroxide being more than 10 ppb or more than 2 ppb, as appropriate.

EXAMPLES

The function and advantages of these and other embodiments can be better understood from the following examples. These examples are intended to be illustrative in nature and are not considered to be limiting the scope of the invention.

Prophetic Example 1

A membrane vacuum degasifier may be used to treat a sample of raw aqueous solution for removal of background dissolved oxygen prior to subjecting the sample to a catalytic hydrogen peroxide destruction. A sample having a dissolved oxygen concentration of 9 ppm (9000 ppb) before removal of oxygen is expected to have a dissolved oxygen concentration of about 2 ppb after degasification. A sample having a hydrogen peroxide concentration of 2 ppb is expected to have a concentration of dissolved oxygen of about 0.94 ppb after catalytic destruction of the hydrogen peroxide. The difference between the two measurements is 47%, which is within the accuracy or resolution of a conventional dissolved oxygen analyzer.

After measuring the $O_2$ concentration, the initial $H_2O_2$ concentration can be calculated by stoichiometry. Calculation of the hydrogen peroxide concentration can be performed with the chemical equation:

$$2H_2O_2 \rightarrow O_2 + 2H_2O.$$

Briefly, one mole of $O_2$ is formed by the complete destruction of two moles of $H_2O_2$. Using the molecular weights of $O_2$ (32 g/mol) and $H_2O_2$ (34 g/mol), the concentration of hydrogen peroxide may be calculated by the following equation:

$$H_2O_2 \text{ (g/L)} = O_2 \text{ (g/L)} \times 2.125$$

Prophetic Example 2

A system for calculation of hydrogen peroxide concentration may be set up as shown in FIG. 2. Briefly, the aqueous solution sample may flow through the vacuum membrane degasifier 310, through valve 420 (valve 422 is closed) to dissolved oxygen analyzer 510. Dissolved oxygen analyzer 510 may measure and record dissolved oxygen concentration $DO_1$. A second sample of the aqueous solution may flow through the vacuum membrane degasifier 310, through the catalytic hydrogen peroxide column 410, (valve 420 is closed), through valve 422 to dissolved oxygen analyzer 510. Dissolved oxygen analyzer 510 may measure and record dissolved oxygen concentration $DO_2$.

The difference between $DO_2$ and $DO_1$ may be determined. To calculate hydrogen peroxide concentration, the difference may be multiplied by 2.125 following the equation:

$$(DO_2 - DO_1) \times 2.125 = H_2O_2.$$

Example 1

Ultrapure water was analyzed with a system as shown in FIG. 2. The system included three Liqui-Cel™ MiniModule™ membrane degasifiers (3M™, Maplewood, MN) arranged in series with $N_2$ used as an inert sweeping gas and a 27 in. Hg vacuum pump. The system included 450 mL of Lewatit® strongly basic, gel-type, palladium-doped, ion exchange resin (Lenntech B.V., Delfgauw, The Netherlands) arranged in a 27 mm polyvinylidene difluoride column. The system included an AMI Oxytrace dissolved oxygen analyzer (Swan Analytical USA, Inc., Wheeling, IL). The water had a temperature of 24.5±0.2° C. The system was run at a flow rate of 200 mL/min.

A test run was performed with oxygen removal and hydrogen peroxide destruction. Dissolved oxygen was measured of the various process streams. A comparative run was performed by the same method without the oxygen removal. The concentration of hydrogen peroxide was calculated by the equation shown in prophetic example 2. The results are presented in Table 1.

TABLE 1

Dissolved Oxygen Concentration of Various Process Streams and Hydrogen Peroxide Calculation

| Sample | Comparative Run | Test run |
|---|---|---|
| Untreated | 2.72 mg/L | 2.72 mg/L |
| After Oxygen Removal | N/A | 7.9 µg/L |
| After Hydrogen Peroxide Destruction | 2.72 mg/L | 17.2 µg/L |
| Difference in Dissolved Oxygen Concentration | 0.00 mg/L | 9.3 µg/L |
| Calculated $H_2O_2$ Concentration | 0.0 mg/L | 19.7 µg/L |

As shown in the results presented in Table 1, the hydrogen peroxide concentration was not detectable without background oxygen removal. However, removal of the background oxygen allowed a concentration of 19.7 ug/L of hydrogen peroxide to be calculated for a similar sample stream. Thus, the concentration of hydrogen peroxide was masked by the concentration of dissolved oxygen in the test run. The methods disclosed herein may be used to calculate hydrogen peroxide concentration in aqueous solutions with a dissolved oxygen background.

Example 2

Ultrapure water was analyzed with a system as described in example 1. The aqueous solution samples tested had a higher concentration of dissolved oxygen. It is noted that the upper limit for the dissolved oxygen analyzer is 20 mg/L.

For this reason, the water samples were diluted in-line with water of a known and constant dissolved oxygen concentration obtain a concentration that is within tolerance of the dissolved oxygen analyzer. The dissolved oxygen concentrations reported in Table 2 were obtained by mass balance calculation.

The results are presented in Table 2.

TABLE 2

Dissolved Oxygen Concentration of Various Process Streams and Hydrogen Peroxide Calculation

| Sample | Comparative Run | Test run |
|---|---|---|
| Untreated | 71.87 mg/L | 71.00 mg/L |
| After Oxygen Removal | N/A | 1.55 μg/L |
| After Hydrogen Peroxide Destruction | 71.20 mg/L | 20.68 μg/L |
| Difference in Dissolved Oxygen Concentration | −0.67 mg/L | 19.13 μg/L |
| Calculated $H_2O_2$ Concentration | Not measurable | 40.65 μg/L |

As shown in the results presented in Table 2, the hydrogen peroxide concentration could not be calculated without background oxygen removal. However, removal of the background oxygen allowed a concentration of 40.65 ug/L of hydrogen peroxide to be calculated for a similar sample stream. Thus, the concentration dissolved oxygen skewed the results in the test run to the extent that the concentration of hydrogen peroxide could not be calculated. The methods disclosed herein may be used to calculate hydrogen peroxide concentration in aqueous solutions with a high dissolved oxygen background.

The phraseology and terminology used herein is for the purpose of description and should not be regarded as limiting. As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Having thus described several aspects of at least one embodiment, it is to be appreciated various alterations, modifications, and improvements will readily occur to those skilled in the art. Any feature described in any embodiment may be included in or substituted for any feature of any other embodiment. Such alterations, modifications, and improvements are intended to be part of this disclosure and are intended to be within the scope of the invention. Accordingly, the foregoing description and drawings are by way of example only.

Those skilled in the art should appreciate that the parameters and configurations described herein are exemplary and that actual parameters and/or configurations will depend on the specific application in which the disclosed methods and materials are used. Those skilled in the art should also recognize or be able to ascertain, using no more than routine experimentation, equivalents to the specific embodiments disclosed.

What is claimed is:

1. A system for determining composition of an aqueous solution, comprising:
    a feed line having a feed inlet fluidly connectable to a source of the aqueous solution comprising a concentration of hydrogen peroxide and a concentration of dissolved oxygen;
    an oxygen removal unit fluidly connected to the feed line downstream from the feed inlet;
    a dissolved oxygen analyzer fluidly connected to the feed line downstream from the oxygen removal unit, the feed line fluidly connecting the feed inlet to the dissolved oxygen analyzer;
    a first conduit fluidly connected to the feed line between the oxygen removal unit and the dissolved oxygen analyzer;
    a hydrogen peroxide removal unit fluidly connected to the first conduit downstream from the oxygen removal unit, the first conduit fluidly connecting the feed inlet to an effluent outlet downstream from the hydrogen peroxide removal unit;
    a second conduit fluidly connected to the first conduit between the hydrogen peroxide removal unit and the effluent outlet, the second conduit extending back to the feed line, the second conduit fluidly connecting the hydrogen peroxide removal unit to the dissolved oxygen analyzer;
    a first valve positioned on the first conduit between the hydrogen peroxide removal unit and the effluent outlet;
    a second valve positioned on the feed line between the oxygen removal unit and the dissolved oxygen analyzer; and
    a control module operably connected to the dissolved oxygen analyzer, the first valve, and the second valve, the control module configured to calculate a concentration of hydrogen peroxide in the source of the aqueous solution from a first concentration of dissolved oxygen measured by opening the second valve to bypass the hydrogen peroxide removal unit and direct the aqueous solution to the dissolved oxygen analyzer and a second concentration of dissolved oxygen measured by closing the second valve to direct the aqueous solution through the first conduit and the hydrogen peroxide removal unit to the dissolved oxygen analyzer, and responsive to the calculated concentration of hydrogen peroxide, the control module further being configured to actuate the first valve to selectively direct the effluent to the effluent outlet or the second conduit.

2. The system of claim 1, further comprising a third valve positioned on the second conduit between the hydrogen peroxide removal unit and the dissolved oxygen analyzer.

3. The system of claim 1, wherein the dissolved oxygen analyzer comprises a display unit configured to display dissolved oxygen concentration.

4. The system of claim 1, wherein the control module is programmed to direct the effluent to the effluent outlet responsive to the calculated concentration of hydrogen peroxide being within about 10 ppb of a target concentration.

5. The system of claim 4, wherein the control module is capable of calculating the concentration of hydrogen peroxide to be about 2 ppb or less.

6. The system of claim 1, wherein the oxygen removal unit comprises at least one of a vacuum degasification unit, a gas transfer membrane, an oxygen scavenging media, and a vacuum mechanical agitation unit.

7. The system of claim 1, wherein the hydrogen peroxide removal unit comprises a catalyst-driven hydrogen peroxide removal unit.

8. The system of claim 7, wherein the catalyst-driven hydrogen peroxide removal unit comprises at least one of a heterogeneous catalyst comprising palladium-doped anion exchange resin, a heterogeneous catalyst comprising platinum immobilized on a substrate, and a homogeneous catalyst comprising an enzyme.

9. A system for determining composition of an aqueous solution, comprising:
  a feed line having a feed inlet fluidly connectable to a source of the aqueous solution comprising a concentration of hydrogen peroxide and a concentration of dissolved oxygen;
  an oxygen removal unit fluidly connected to the feed line downstream from the feed inlet;
  a first dissolved oxygen analyzer fluidly connected to the feed line downstream from the oxygen removal unit, the feed line fluidly connecting the feed inlet to the first dissolved oxygen analyzer;
  a first conduit fluidly connected to the feed line downstream from the oxygen removal unit;
  a hydrogen peroxide removal unit fluidly connected to the first conduit downstream from the oxygen removal unit, the first conduit fluidly connecting the feed inlet to an effluent outlet downstream from the hydrogen peroxide removal unit;
  a second dissolved oxygen analyzer fluidly connected to the first conduit downstream from the hydrogen peroxide removal unit;
  a second conduit fluidly connected to the first conduit between the hydrogen peroxide removal unit and the effluent outlet, the second conduit extending back to the feed line;
  a first valve positioned on the first conduit between the hydrogen peroxide removal unit and the effluent outlet;
  a second valve positioned on the feed line downstream from the oxygen removal unit; and
  a control module operably connected to the first dissolved oxygen analyzer, the second dissolved oxygen analyzer, the first valve, and the second valve, the control module programmed to calculate a concentration of hydrogen peroxide in the source of the aqueous solution from a first concentration of dissolved oxygen measured by the first dissolved oxygen analyzer and a second concentration of dissolved oxygen measured by closing the second valve to direct the aqueous solution through the first conduit and the hydrogen peroxide removal unit to the second dissolved oxygen analyzer and responsive to the calculated concentration of hydrogen peroxide, the control module further being configured to actuate the first valve to selectively direct an effluent from the hydrogen peroxide removal unit to the effluent outlet or the second conduit.

10. The system of claim 9, wherein the first and second dissolved oxygen analyzers comprise a display unit configured to display dissolved oxygen concentration.

11. The system of claim 9, wherein the control module is programmed to direct the effluent to the effluent outlet responsive to the calculated concentration of hydrogen peroxide being within about 10 ppb of a target concentration.

12. The system of claim 11, wherein the control module is capable of calculating the concentration of hydrogen peroxide to be about 2 ppb or less.

13. The system of claim 9, wherein the oxygen removal unit comprises at least one of a vacuum degasification unit, a gas transfer membrane, an oxygen scavenging media, and a vacuum mechanical agitation unit.

14. The system of claim 9, wherein the hydrogen peroxide removal unit comprises a catalyst-driven hydrogen peroxide removal unit.

15. The system of claim 14, wherein the catalyst-driven hydrogen peroxide removal unit comprises at least one of a heterogeneous catalyst comprising palladium-doped anion exchange resin, a heterogeneous catalyst comprising platinum immobilized on a substrate, and a homogeneous catalyst comprising an enzyme.

* * * * *